(12) United States Patent
Berliner

(10) Patent No.: US 6,181,768 B1
(45) Date of Patent: Jan. 30, 2001

(54) RADIOLOGICAL IMAGE ACQUISITION AND MANIPULATION SYSTEM FOR MULTIPLE VIEW STEREOSCOPIC IMAGING

(76) Inventor: Leonard F. Berliner, 18 Carol Ct., Staten Island, NY (US) 10309

(*) Notice: Under 35 U.S.C. 154(b), the term of this patent shall be extended for 0 days.

(21) Appl. No.: 09/325,909

(22) Filed: Jun. 4, 1999

(51) Int. Cl.$^7$ ..................................................... A61B 6/02
(52) U.S. Cl. ............................. 378/41; 600/429; 128/916
(58) Field of Search ............................. 378/41; 600/443, 600/429, 425; 128/916

(56) References Cited

U.S. PATENT DOCUMENTS

| | | |
|---|---|---|
| 688,458 | 12/1901 | Caldwell . |
| 4,544,949 | 10/1985 | Kurihara ............................ 358/111 |
| 4,627,087 | 12/1986 | Marks ..................................... 378/4 |
| 4,819,255 | 4/1989 | Sato ..................................... 378/42 |
| 5,090,038 | 2/1992 | Asahina ................................ 378/41 |
| 5,155,750 | 10/1992 | Klynn et al. ........................ 378/42 |
| 5,233,639 | 8/1993 | Marks ................................... 378/42 |
| 5,261,404 | * 11/1993 | Mick et al. ......................... 128/916 |
| 5,488,952 | * 2/1996 | Schoolman ......................... 128/916 |
| 5,493,595 | * 2/1996 | Schoolman ........................... 378/41 |
| 5,961,456 | * 10/1999 | Gildenberg ......................... 600/429 |

* cited by examiner

Primary Examiner—David V. Bruce
Assistant Examiner—Pamela R. Hobden
(74) Attorney, Agent, or Firm—Goldstein & Canino

(57) ABSTRACT

A radiological imaging system, for providing a viewer with multiple stereoscopic radiological views of a patient from a single pair of acquired images, comprising acquiring a first image and second image to achieve a properly matched stereoscopic pair. The stereoscopic pair is presented to the viewer by presenting the first image to the left eye and the second image to the right eye. The images are then manipulated by performing at least one of swapping the first image and second image, and flipping horizontally the first image and second image. The resulting manipulated images are presented to the viewer to provide at least one distinct stereoscopic view which provides the viewer with an additional perspective on the patient. Accordingly, at least stereoscopic anterior and posterior views can be achieved using a single matched pair of images.

6 Claims, 3 Drawing Sheets

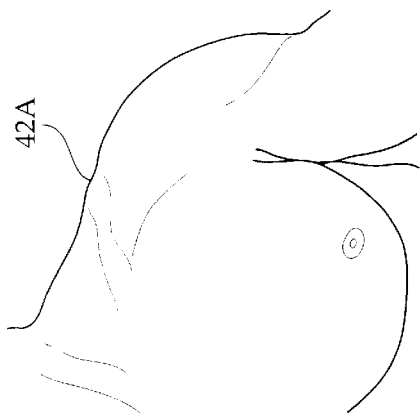
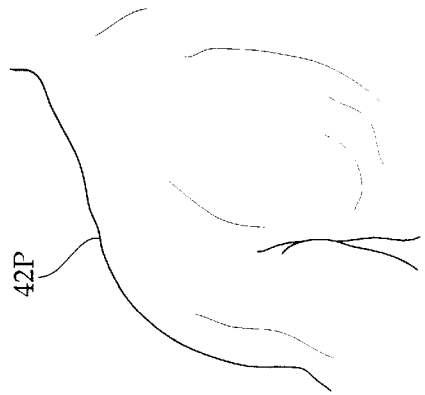
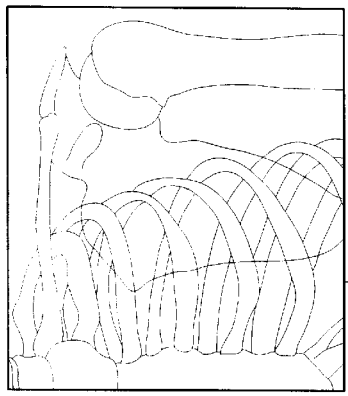
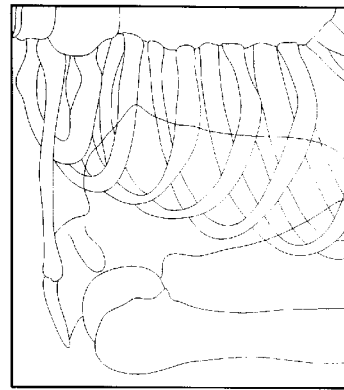
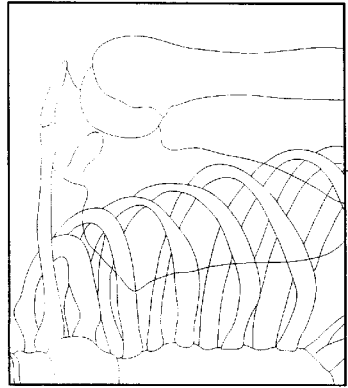
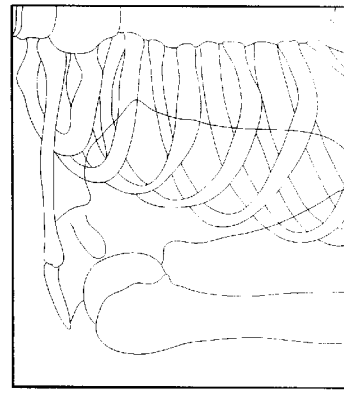
FIG. 4
FIG. 5

RADIOLOGICAL IMAGE ACQUISITION AND MANIPULATION SYSTEM FOR MULTIPLE VIEW STEREOSCOPIC IMAGING

BACKGROUND OF THE INVENTION

The invention relates to a radiological image acquisition manipulation system for multiple view stereoscopic imaging. More particularly, the invention relates to a system for acquiring radiological images of a patient, manipulating said images, and presenting said manipulated images in a manner which presents a viewer with multiple discrete stereoscopic views of a patient.

X-rays or Radiographs may be thought of as an image composed of superimposed and overlapping shadows, created on a detector or film, after the x-rays have passed through a portion of a patient. The interpretation of these overlapping shadows requires many years of training. Any process which helps to clarify an x-ray or present that image in a way that is more easily interpreted is a tremendous aid to the Radiologist and can help the Radiologist make a more accurate and reliable diagnosis for the patient.

The phenomenon of monocular human vision is complex enough without considering the neurophysiology of binocular vision. For normal monocular vision to take place the eye is presented with light from the real world. An image is then focused by the lens onto the retina, stimulating neural impulses via the optic nerve, which then stimulate the visual cortex in the occipital lobe of the brain. Thereby, the brain perceives a 2-dimensional image of the scene.

In binocular, stereoscopic vision, each eye contributes one of 2 views of the same scene, with just the right amount of angular misregistration, or parallax. The two slightly incongruous images presented to the right and left occipital lobes are then fused through a complex neurophysiological process into a single scene in which true, 3-dimensional depth information is perceived by the viewer.

Stereoscopic radiography, however, fell into disfavor due to recognition of the dangers of ionizing radiation (since 2 exposures are required for 1 stereoscopic image) and due to the cumbersome nature of the equipment required to view the stereo pairs.

More recent attempts at applying stereoscopic imaging to radiography centered around using either two x-ray tubes, a specialized dual focal-spot x-ray tube, or a single, rotating x-ray tube to acquire the stereoscopic pairs of images. These techniques have made use of image intensifiers, video technology, analog-to-digital conversion, and various visual display techniques to more effectively create stereoscopic fluoroscopy and angiography.

As sophisticated as these techniques are, however, they still duplicate the type of stereoscopic pairs that were created in the early part of the 20th century. There are no previous examples in the art, of a technique to manipulate and exploit the anatomic, spatial, and pathologic data inherent in the images themselves.

Further, none of these techniques provide the viewer with multiple stereoscopic views obtained from a single pair of acquired images.

While these units may be suitable for the particular purpose employed, or for general use, they would not be as suitable for the purposes of the present invention as disclosed hereafter.

SUMMARY OF THE INVENTION

It is an object of the invention to provide an imaging process which presents a viewer with anatomical relationships and pathological processes in a way which cannot be seen using other techniques. Accordingly, multiple three-dimensional views are presented to the viewer, which provide the experienced radiological specialist with additional insight concerning the patient which could not otherwise be discerned from an ordinary two-dimensional X-ray image. By presenting the same stereographic images in different ways, the radiological specialist can derive meaning from the images which would not ordinarily be perceived from a single view angle.

It is another object of the invention to provide an imaging process which does not subject the patient to additional radiation exposure in order to provide the viewer with additional views. Accordingly, the present invention provides additional view angles without requiring the acquisition of additional X-ray images.

It is a further object of the invention to provide an imaging process which assist with a multitude of diverse medical procedures. Accordingly, the present imaging technique is useful not only for a variety of diagnostic studies, but also for a large variety of invasive and interventional procedures.

It is a still further object of the invention that the imaging process can be employed not only with static x-ray images, but with paired X-rays taken of a moving subject or with a moving camera. Accordingly, angiographic images can be presented in three dimensions from different perspectives to provide the viewer with previously unseen detail.

The invention is a radiological imaging system, for providing a viewer with multiple stereoscopic radiological views of a patient from a single pair of acquired images, comprising acquiring a first image and second image to achieve a properly matched stereoscopic pair. The stereoscopic pair is presented to the viewer by presenting the first image to the left eye and the second image to the right eye. The images are then manipulated by performing at least one of swapping the first image and second image, and flipping horizontally the first image and second image. The resulting manipulated images are presented to the viewer to provide at least one distinct stereoscopic view which provides the viewer with an additional perspective on the patient. Accordingly, at least stereoscopic anterior and posterior views can be achieved using a single matched pair of images.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

FIG. 4 illustrates a pair of stereoscopic images, which have been swapped, so that they will provide what appears to be a posterior view of the contralateral shoulder.

FIG. 5 illustrates a pair of stereoscopic images, which have been swapped and flipped horizontally, so that they provide to the viewer what appears to be a posterior view of the ipsilateral shoulder.

DETAILED DESCRIPTION OF THE PREFERRED EMBODIMENTS

Figure 1:
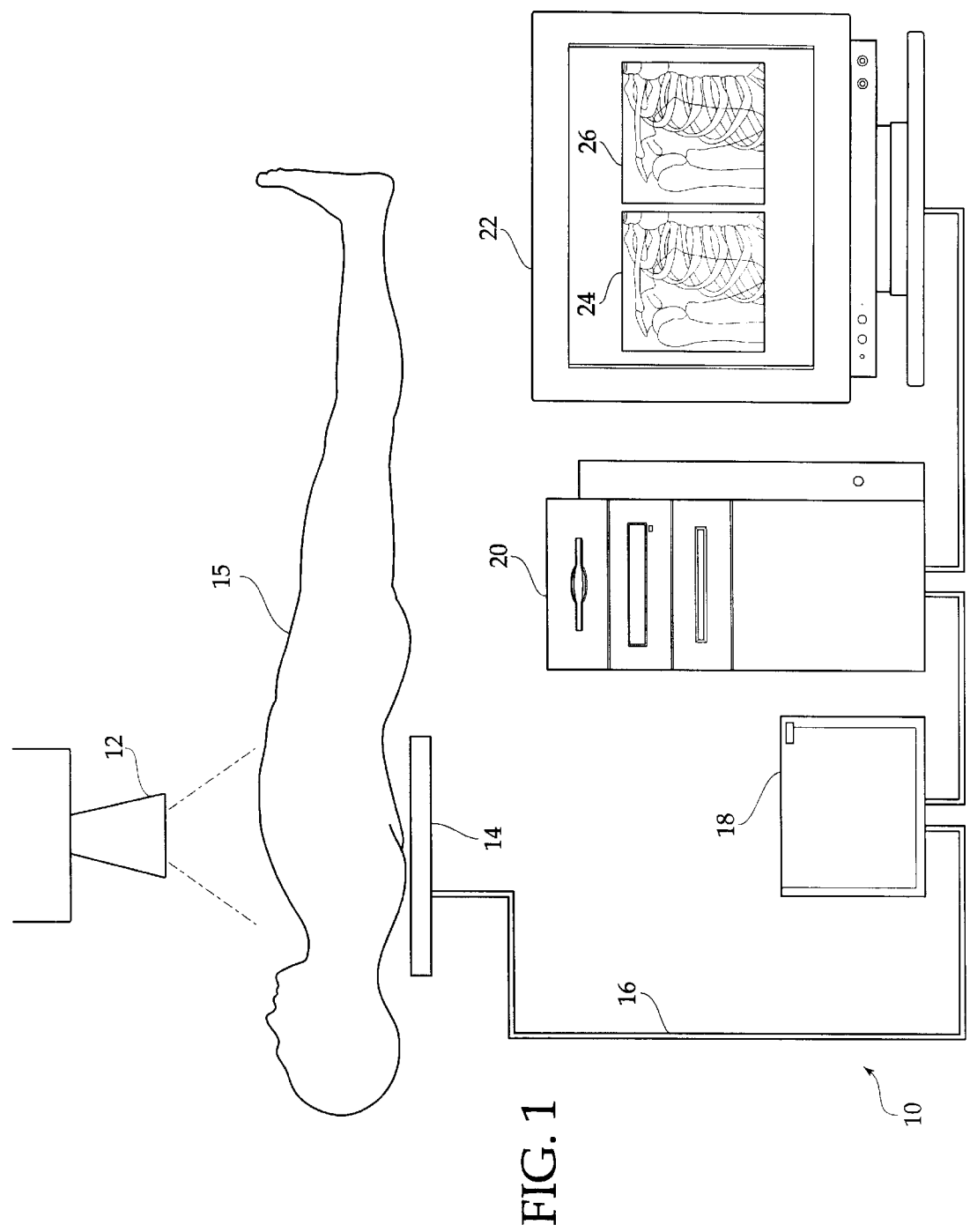
FIG. 1 illustrates image acquisition, manipulation, and presentation apparatus used in practicing the system of the present invention.

FIG. 1 illustrates an imaging apparatus 10, comprising an X-ray source 12 and a detector 14. A patient 15 is interposed between the X-ray source 12 and detector 14. The detector 14 produces an output 16 which varies according to the relative transmissibility of different portions of the patient 15. An Analog to Digital converter 18, digitizes the output 16 from the detector 14, and produces digital data which is captured by a computer workstation 20.

According to the present invention, the imaging apparatus 10 must capture a first image and a second image. The first image and second image should be angularly separated by between two and ten degrees to provide the required parallax necessary to mimic binocular vision. This angular separation can be achieved by moving the detector or moving the patient. The X-ray source 12 may comprise two X-ray tubes aimed at the detector, wherein the two X-ray tubes form an angle of between two and ten degrees. Alternatively, this angular separation can be achieved by acquiring successive temporal images of a moving organ—such as a pumping heart—by precisely timing the temporal separation between images as the subject organ moves, so that an appropriate angular separation between images is achieved.

The images acquired by the computer workstation 20 may be viewed by a viewer on a display 22. The viewer has a left eye and a right eye. The display is configured to provide a left image 24 and a right image 26 to the left eye and right eye of the viewer, respectively. Image delivery to the appropriate eye may be accomplished in a variety of ways, including through the use of shutter glasses, through a autostereoscopic flat panel display without shutter glasses, or any other suitable conventional manner of delivering two distinct images to the left eye and right eye, as is well known in field of three-dimensional imaging.

Initially it should be noted that X-rays differ from standard photographs, in that standard photographs only provide data concerning the surface of the subject. Light reflected off the subject surface creates patterns of light and dark which provide the viewer with visual cues regarding surface contours and textures. In contrast, an X-ray image contains data representing an infinite number of planes extending through the subject patient. It takes a skilled eye to discern the various planes and locate the relevant information from the image.

FIG. 2 through FIG. 5 present different views which may be obtained by manipulating the first image 31 and second image 32 according to the present invention. The different views allow the viewer to perceive the object, i.e. the patient, in different ways. Visual cues, which are ordinarily interpreted by a radiological professional, will be more or less apparent in certain views than in others. The actual difference between the viewers perception of the views is largely psychological, but will vary wherein certain features of the patient will be more apparent or easier to perceive in some views, compared to others.

Figure 2:
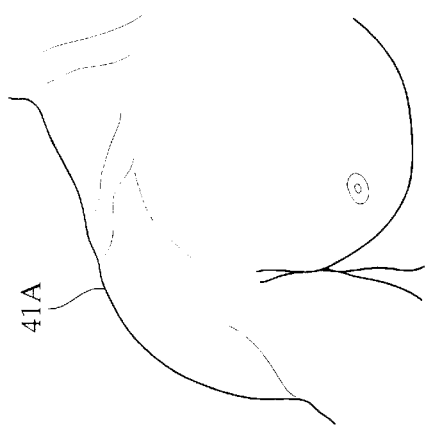
FIG. 2 illustrates a depiction of a pair of stereoscopic images, which when viewed by the left and right eye of the viewer as shown will provide the viewer with what appears to be an anterior view of the ipsilateral shoulder.
Figure 2:
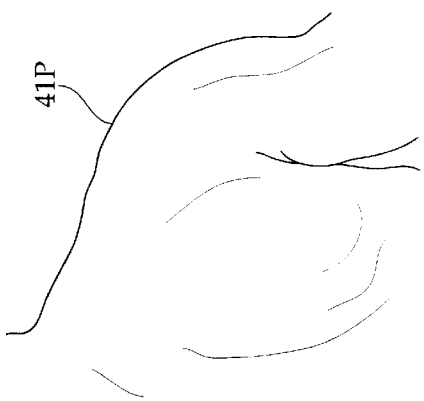
Figure 2:
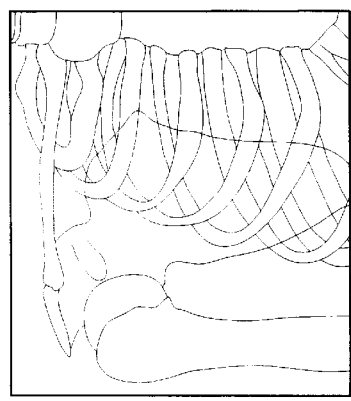
Figure 2:
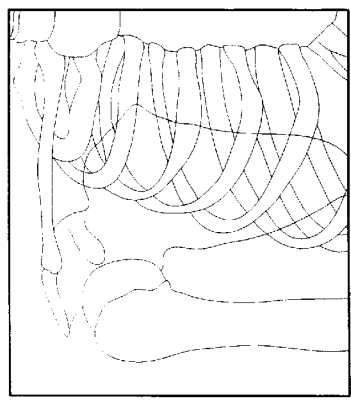

In particular, FIG. 2 illustrates the first image 31 and second image 32 displayed naturally, without modification, wherein the first image 31 is directed to the left eye, and the second image 32 is directed to the right eye. The viewer thus perceives an anterior view of an ipsilateral shoulder of the patient 41A.

Figure 3:
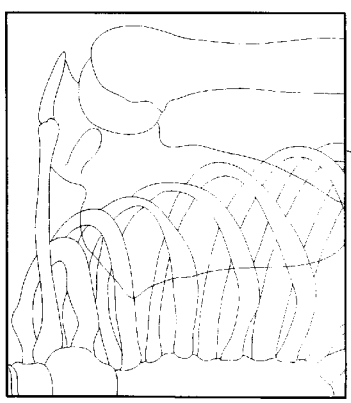
FIG. 3 illustrates a pair of stereoscopic images, which have been flipped horizontally, so that when presented to the viewer they will provide what appears to be a posterior view of the ipsilateral shoulder.
Figure 3:
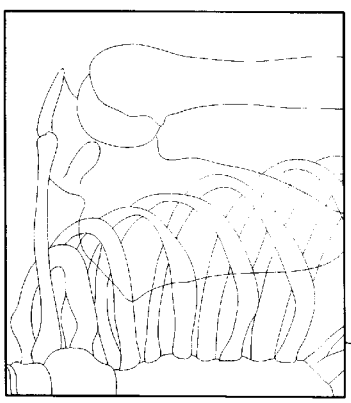

In FIG. 3, the first image 31 and second image 32 have been manipulated, wherein each of the first image 31 and second image 32 have been flipped horizontally, about the y-axis. However, the first image 31 and second image 32 are still in their natural positions, directed to the left eye and right eye, respectively. Accordingly, the viewer perceives what appears to be a posterior view of the ipsilateral shoulder 41P.

It is important to note that had the first image and second image been ordinary photographic images, the modification of FIG. 3 would be completely unviewable. In fact when ordinary photographic images are used, display of anything other than true, properly paired, non-reversed and non-transposed, conventional stereoscopic images results in a phenomenon called a pseudo-stereoscopic image. Due to the unreconcilable data inherent in the images of the surface structures, unpredictable portions of the foreground recede and portions of the background advance to the viewer in an unnatural way. Since the pseudo-stereoscopic image is optically confusing, it is unusable for accurate stereoscopic portrayals of a photographic subject. Thus, there is no analogous use of the present invention with standard three-dimensional photography. Accordingly, it is an unexpected result that this manipulation results in a useful, and even useful composite three dimensional image.

In FIG. 4, the first image 31 and second image 32 have been swapped to create another view. In other words, the first image 31 is directed to the right eye, and the second image 32 is directed to the left eye. Symbolically, the positions of the first image 31 and second image 32 in FIG. 4 have been swapped. The viewer now perceives what appears to be a posterior view of the contralateral shoulder 42P.

In FIG. 5, the first image 31 and second image 32 have been swapped, and the first image 31 and second image 32 have each been flipped horizontally to create yet another view. The flipped first image 31 is thus directed to the right eye, and the flipped second image 32 is thus directed to the left eye. Accordingly, the viewer now perceives what appears to be an anterior view of the contralateral shoulder 42A.

Specific radiological application for the multiple stereoscopic viewing technique described are innumerable. However, a few examples of its usefulness are provided hereinafter.

In orthopedic radiology, multiple viewing angles are useful for evaluating fractures and dislocations, locating foreign bodies, and aligning bone fragments and prostheses. Having anterior and posterior stereoscopic views of the same subject can be extremely useful in accomplishing any of these goals.

In Maxillofacial surgery, the techniques of the present invention are useful for surgical planning, for intra-operative surgical guidance, and to evaluate facial structure and symmetry. In particular, horizontal flipping of the images results in a useful posterior view of the facial bones and mandible. Further, flipping and swapping the images provides a view of one side which may be directly compared to a half image of the other side to achieve greater symmetry than can be achieved with routine imaging techniques. of course numerous other examples exist presently, and will be developed in time which further show the benefits of the present inventive system. Therefore, in conclusion, herein is presented a system for providing multiple stereoscopic views from a single pair of acquired radiological images.

What is claimed is:

1. A radiological imaging system, for providing multiple stereoscopic viewing perspectives of a patient to a viewer, comprising the steps of:

acquiring a pair of radiological images of the patient, comprising a first image and a second image;

presenting a standard view of the patient by presenting the first image and second image to the viewer by presenting the first image to the left eye of the viewer and the second image to the right eye of the viewer, wherein the viewer thus perceives a stereoscopic view of the patient;

manipulating the first image and second image by performing at least one of swapping the first image and second image, and flipping the first image and second image horizontally; and presenting a distinct view of the patient to the viewer by presenting the manipulated first image and second image to the viewer by providing the first image to the left eye of the viewer and the second image to the right eye of the viewer.

2. The radiological imaging system as recited in claim 1, wherein the step of manipulating the first image and second image comprises both swapping the first image and second image, and flipping the first image and second image horizontally.

3. A radiological imaging system, for providing multiple views from a single pair of properly matched stereoscopic images, including a first image intended to be viewed by the left eye, and a second image intended to be viewed by the right eye, comprising the steps of:

swapping the first image and second image; and viewing the first image by the left eye and the second image by the right eye.

4. The radiological imaging system as recited in claim 3, wherein the step of viewing is preceded by flipping horizontally the first image and flipping horizontally the second image.

5. A radiological imaging system, for providing multiple views from a single pair of properly matched stereoscopic images, including a first image intended to be viewed by the left eye, and a second image intended to be viewed by the right eye, comprising the steps of:

flipping horizontally the first image;

flipping horizontally the second image; and viewing the first image by the left eye and the second second by the right eye.

6. The radiological imaging system as recited in claim 5, wherein the step of viewing is preceded by swapping the first image and the second image.

* * * * *